United States Patent
Chow

(10) Patent No.: US 7,991,456 B2
(45) Date of Patent: Aug. 2, 2011

(54) SYSTEMS AND METHODS FOR MANAGING HEART RATE DEPENDENT CONDITIONS

(75) Inventor: Theodore Chow, Mason, OH (US)

(73) Assignee: Medtronic, Inc., Minneapolis, MN (US)

( * ) Notice: Subject to any disclaimer, the term of this patent is extended or adjusted under 35 U.S.C. 154(b) by 347 days.

(21) Appl. No.: 12/193,337

(22) Filed: Aug. 18, 2008

(65) Prior Publication Data

US 2009/0048529 A1   Feb. 19, 2009

Related U.S. Application Data

(60) Provisional application No. 60/965,133, filed on Aug. 16, 2007.

(51) Int. Cl.
*A61N 1/00*   (2006.01)
(52) U.S. Cl. .............. 600/509; 600/517; 607/25
(58) Field of Classification Search .......... 600/508–521; 607/4–28
See application file for complete search history.

(56) References Cited

U.S. PATENT DOCUMENTS

| | | | |
|---|---|---|---|
| 5,749,900 A | | 5/1998 | Schroeppel et al. |
| 5,836,971 A | * | 11/1998 | Starkweather .................. 607/4 |
| 5,882,352 A | * | 3/1999 | Duncan et al. .................. 607/4 |
| 7,181,270 B2 | | 2/2007 | Breithardt et al. |
| 2004/0215265 A1 | | 10/2004 | Keizer |

FOREIGN PATENT DOCUMENTS

EP   0 596 598   5/1994

OTHER PUBLICATIONS

Search Report and Written Opinion from corresponding PCT Application Serial No. PCT/US2008/009836 mailed Nov. 17, 2008 (14 pages).
International Preliminary Report on Patentability from corresponding PCT Application Serial No. PCT/US2008/009836 mailed Feb. 25, 2010 (9 pages).
European Office Action from corresponding European Application Serial No. 08795414.5 dated Sep. 13, 2010 (4 pages).
European Response filed on Mar. 22, 2011 for corresponding European Patent Application No. 08795414.5 (6 pages).

* cited by examiner

*Primary Examiner* — Scott M Getzow
(74) *Attorney, Agent, or Firm* — Shumaker & Sieffert, P.A.

(57) ABSTRACT

Systems and methods are provided for monitoring a cardiac condition of a patient. The system includes a sensor for receiving a patient's heart rate and a processor that is programmable to set a patient's safe heart rate zone. The processor is also configured to determine whether the patient's heart rate has exceeded the safe heart rate zone. In response to determining that the patient's heart rate has exceeded the safe heart rate zone, the processor may reprogram a new safe heart rate zone.

45 Claims, 5 Drawing Sheets

SYSTEMS AND METHODS FOR MANAGING HEART RATE DEPENDENT CONDITIONS

CROSS REFERENCE TO RELATED APPLICATIONS

This application claims the benefit of U.S. Provisional Application Ser. No. 60/965,133, filed Aug. 16, 2007, the entire contents of which are incorporated herein by reference.

BACKGROUND OF THE INVENTION

Use of implantable medical devices (IMDs) is ubiquitous in treating cardiac diseases. These IMDs analyze cardiac electrical activity of a patient to monitor and assess their cardiac condition. For example, many patients who are at risk of cardiac ischemia have pacemakers or implantable cardioverter/defibrillators (ICDs). These IMDs sense the cardiac activity of the patient and stimulate the patient's heart by providing electrical pulses to restore the heart rate to a normal rhythm. Oftentimes, once the IMD detects an abnormal cardiac activity, the IMD takes an action to correct the abnormal incident either by sending pulses to the patient's heart or alerting a clinician or dispensing a drug if applicable.

Many of these devices analyze various characteristics of electrocardiogram (ECG), such as the T wave and ST segments. However, there exist certain drawbacks when using these characteristics of ECG for monitoring the overall cardiac condition of a patient. First, such data acquired from an implantable device may not be equivalent to data acquired using external ECG electrodes (e.g., during "routine" cardiac stress testing or T wave alternans testing). As such, clinical interpretation based upon data acquired through an implantable device may be misleading if such interpretation is referenced to knowledge garnered from studies involving externally acquired data (i.e. using surface ECG electrodes). For example, 2 microvolts of T wave alternans obtained through an internal device is, in fact, known to be not equivalent to 2 microvolts of T wave alternans measured through surface ECG electrodes. The amplitude of measured alternans increases as one goes below the surface of the skin to measure it. Moreover, internally acquired ECG signals through an implantable device suffer from limitations relating to the fact that the number of discrete ECG vectors that can be used are severely limited in comparison to measurement using external ECG electrodes. This is an intrinsic limitation of every approach that seeks to use internally measured ECG phenomenon (such as T wave alternans and ischemia) as the principal method of diagnosis. Since it is well known that such phenomenon may be seen in one vector but not another, and since the range of vector analysis through an internal device is more limited than using the external electrodes in which multiple vectors are used, diagnosis by external electrodes (assuming equivalent sensitivity for each vector) is preferred as it will result in less "under-detection". Therefore, making a clinical diagnosis based on external ECG measurement may reduce under-detection of cardiac diseases.

As shown, the implantable devices which use internally detected ECG phenomenon (e.g. T wave alternans and ST segment changes) as the principal means for detecting clinically significant physiological processes (e.g. ventricular arrhythmic substrate and cardiac ischemia) are intrinsically limited in that they: a) may under-detect the phenomenon or physiological process of interest, b) may produce an output result that is misleading because it is not equivalent to the same result obtained using traditional ECG electrodes which clinicians are more familiar with and for which there is much more clinical data to guide therapy.

Some implantable devices contain software that detects heart rate (HR) and/or pathologic cardiac rhythms (i.e. cardiac arrhythmias), and subsequently delivers this information to clinicians. However, while these devices are able to detect and even treat these pathologic heart rhythms, they do not guide the physician along a clinical strategy for preventing these cardiac arrhythmias in the first place—they are reactive rather than preventative. This latter fact exposes patients to greater risk than a strategy that prevents arrhythmia (or ischemia) in the first place. The fact that T wave alternans and cardiac ischemia may both be heart rate dependant phenomenon (i.e. become present at higher heart rates) makes heart rate monitoring a useful approach to prevent and/or diagnose those conditions.

SUMMARY OF THE INVENTION

There is a need for an effective approach that bridges the limitations of internally measured ECG phenomenon with the strength of conventional external ECG testing, and applied in a manner that shifts the objectives from diagnosis of abnormal phenomenon (T wave alternans and ST segment depression) or physiology (ventricular arrhythmic substrate and ischemia) to prevention of these phenomenon and physiologic conditions. This approach, emphasizing prevention, reduces the risk of clinical complications and optimizes patient health and safety in a manner that existing methods that emphasizes detection do not.

The cardiac monitoring system described herein addresses various deficiencies in the prior art by, in various embodiments, providing improved systems and methods for identifying a safe heart rate zone and maintaining the HR within the identified safe HR zone aided by the IMD. In one embodiment, the implantable system includes a sensor for receiving a patient's heart rate and a processor coupled to the sensor. The processor, being programmable to set a patient's safe heart rate zone, is configured to determine whether the patient's heart rate has exceeded the safe heart rate zone. The processor, in response to determining that the patient's heart rate has exceeded the safe heart rate zone, reprograms a new safe heart rate zone. In some embodiments, the processor wirelessly transmits to a clinician the patient's heart rate when the heart rate exceeds the safe heart rate zone. In some embodiments, the processor alerts a clinician or patient when drift occurs in the safe heart rate zone.

In some embodiments, the implantable system includes a memory for storing the duration of time that the patient has been outside the safe heart rate zone and a transceiver for sending an alert to a patient or a clinician and receiving information from the clinician. The received information from the clinician includes information for readjusting the patient's safe heart rate zone.

In some embodiments, the safe rate zone is defined by a patient's heart rate at above which the risk of adverse cardiac condition clinically increases. In other embodiments, the safe rate zone is defined by a patient's heart rate at above which abnormal changes to the ECG occur.

In another aspect, the invention provides a method of managing a heart rate dependent medical condition including programming a processor of an implantable medical device with a patient's safe heart rate zone, sensing a patient's heart rate with the implantable medical device, comparing the patient's heart rate to the safe heart rate zone and determining whether the patient's heart rate has exceeded the safe heart rate zone, and in response to determining that the patient's heart rate has exceeded the safe heart rate zone, reprogramming the implantable medical device with a new safe heart rate zone. In some embodiments, the method includes transmitting to a remote terminal the result of the comparison between the patient's heart rate and the safe heart rate zone or alerting a clinician when the patient's heart rate falls outside of the safe heart rate zone. In response to the alert, in some embodiments, the method includes retesting the patient using a standard technique for evaluating the overall cardiac condition of the patient. The standard technique may include a test using surface ECG electrodes. In some embodiments, the method reprograms the safe heart rate zone only when the surface ECG electrode test confirms that the patient has significant T wave alternans within the current safe heart rate zone. The method may also modify a medical therapy to maintain the patient's heart rate within the safe heart rate zone.

For managing cardiac arrest, the method includes determining the increased risk of cardiac arrest by observing daily heart rate in excess of the onset heart rate for significant T wave alternans. The risk of cardiac arrest is indicated by a decrease in the difference between the patient's daily heart rate and a maximum negative heart rate. In some embodiments, the risk of cardiac arrest is indicated by an overlap between daily heart rate and a maximum negative heart rate.

For managing cardiac ischemia, the method includes an upper heart rate that defines the safe heart rate zone is determined by observing the heart rate at which clinical ischemia develops during stress testing. The method also includes modifying a medical therapy based on data received from the implantable medical device to maintain the patient's heart rate within the safe heart rate zone. In some embodiments, the method includes determining increased amount of cardiac ischemia and the risk of cardiac ischemia by observing increased heart rate adjusted T wave alternans.

For managing heart failure, the method includes determining potential progression of heart failure by observing increased heart rate adjusted T wave alternans. The method may include alerting a clinician when the patient's heart rate falls outside the safe heart rate zone.

In some embodiments, the method for managing a heart rate dependent medical condition includes determining a drift in the safe heart rate zone by observing changes in a surrogate marker measured by the implantable medical device. For arrhythmias the surrogate marker is implantable medical device measured T wave alternans. For ischemia the surrogate marker is implantable medical device measured ST segment deviation.

In some embodiments, the methods for managing a heart rate dependent medical condition includes displaying a risk burden value of a patient by determining the proportion of time that the patient's heart rate is outside the safe heart rate zone and plotting the risk burden value against time.

In another aspect, the invention provides a computer readable medium encoding instructions for causing a computer to carry out a method including programming a processor of an implantable medical device with a patient's safe heart rate zone, sensing a patient's heart rate with the implantable medical device, comparing the patient's heart rate to the safe heart rate zone and determining whether the patient's heart rate has exceeded the safe heart rate zone, and in response to determining that the patient's heart rate has exceeded the safe heart rate zone, reprogramming the implantable medical device with a new safe heart rate zone. The computer readable medium may also include instructions for alerting a clinician when the patient's heart rate falls outside of the safe heart rate zone. In some embodiments, the computer readable medium also includes instructions for retesting the patient, in response to the alert, using a surface ECG based test for evaluating the overall cardiac condition of the patient. In some embodiments, the computer readable medium includes instructions for reprogramming the safe heart rate zone only when the treadmill test confirms that the patient has significant T-wave alternans within the current safe heart rate zone. The computer readable medium may also include modifying a medical therapy to maintain the patient's heart rate within the safe heart rate zone.

BRIEF DESCRIPTION OF THE DRAWINGS

The following figures depict illustrative embodiments of the invention in which like reference numerals refer to like elements. These depicted embodiments may not be drawn to scale and are to be understood as illustrative of the invention and not as limiting.

Further features and advantages of the present invention will be apparent from the following description of exemplary embodiments and from the claims.

DESCRIPTION OF CERTAIN ILLUSTRATED EMBODIMENTS

To provide an overall understanding of the invention, certain illustrative embodiments will now be described, including exemplary embodiments of a device that is used in patient's heart rate monitoring and management. The systems and methods described herein may be adapted and modified for other suitable applications and that such other additions and modifications will not depart from the scope hereof.

A device identifying a patient specific safe heart rate zone and monitoring the patient's heart rate (HR) against the safe heart rate zone may allow a clinician to titrate medical therapy under a continuous heart rate surveillance to maintain HR within a specified safe HR zone.

Figure 1:
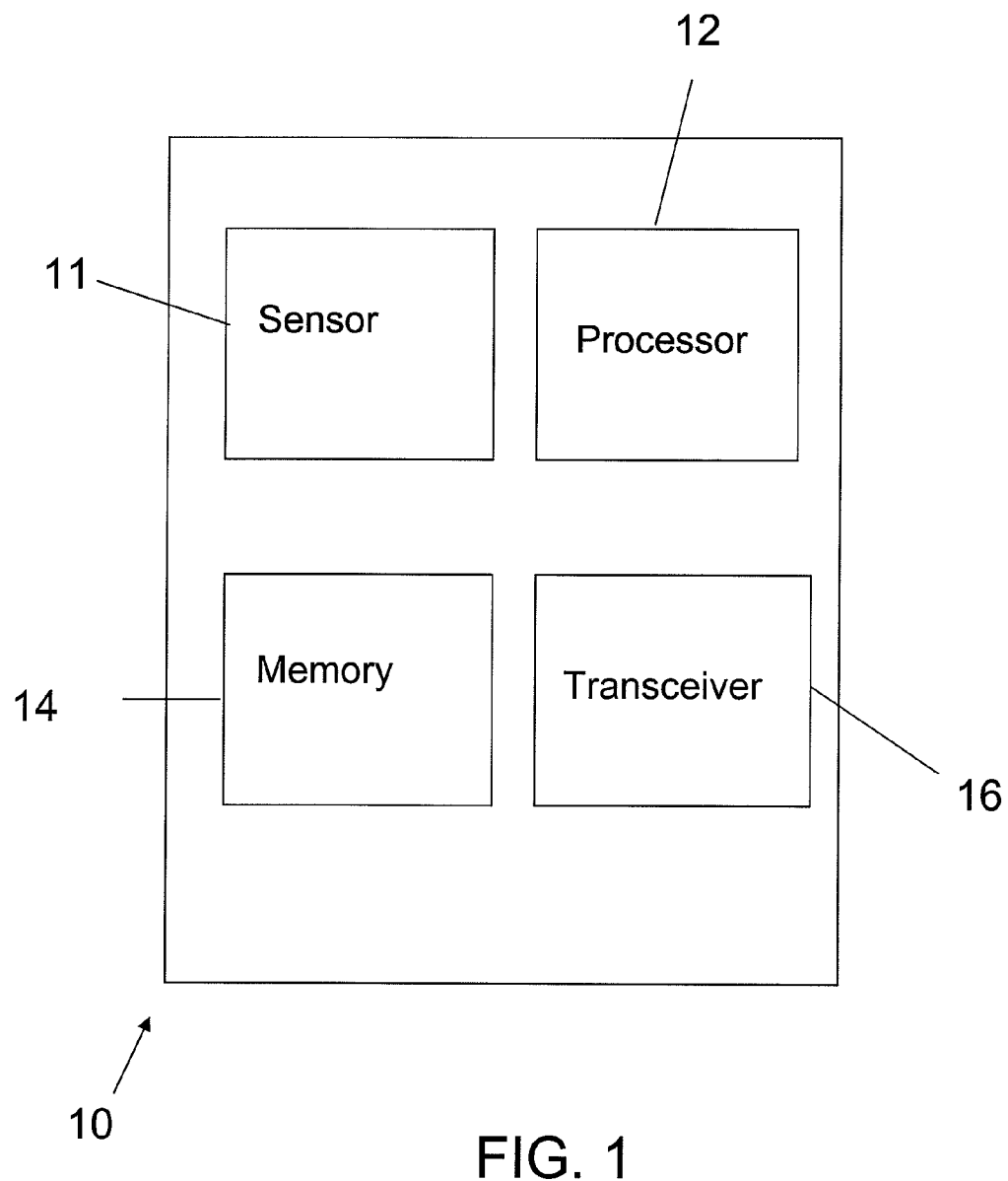
FIG. 1 is a diagram illustrating an embodiment of an implantable medical device for identifying and monitoring a safe heart rate zone.

Turning to the illustrative embodiments, FIG. 1 illustrates a diagram of an implantable medical device 10 for measuring and monitoring the patient's HR. The processor 12 of the IMD 10 is programmable to set a patient's safe HR zone. The IMD 10 includes a sensor 11 for receiving and monitoring the patient's heart rate and a processor 12 for comparing the patient's daily HR to the defined safe HR zone of the patient. In certain embodiments, the IMD 10 may be a pacemaker, an implantable loop recorder, or an implantable cardioverter-defibrillator (ICD) including Bi-ventricular ICD.

FIG. 1 shows the IMD 10 further including a memory 14 connected to the processor 12 to store daily heart rate related information and a transceiver 16 connected to the processor 12 to send an alert or information stored in the memory 14 to a clinician and to receive data from a clinician. In one embodiment, the processor 12 is programmed to alert the patient or the clinician when the patient's HR deviates from the safe HR zone. Via the transceiver 16, the IMD may be linked to a remote terminal where information such as patient HR data may be sent according to a specified schedule or upon the patient's heart rate exceeding the safe zone. The IMD 10 may store heart rates that are within and outside the safe HR zone. The IMD 10 may also be in communication with a device that emits audible sounds or signals to alert the patient or clinician if the HR exceeds the safe zone threshold. In addition to alerting the patient or a clinician when the patient's heart rate exceeds the safe HR zone, the processor 12 is also configured to reprogram a new safe HR zone.

In some embodiments the processor 12 is configured to detect, based on the internally recorded ECG data, whether the safe HR zone is shifting or has shifted. In response to detecting such change in the safe HR zone, the processor 12 alerts the patient or the clinician. More specifically, the IMD 10 may monitor for TWA or ST segment depression, and if it notices a change in these findings the device may send an alert to the patient or physician to prompt evaluation and reprogramming of the safe HR zone. In some embodiments, the safe HR zone is reprogrammed after re-testing for TWA or ischemia using external ECG electrode-based techniques (e.g. treadmill TWA or stress testing). The IMD 10, after detecting a change in the safe HR zone, may automatically re-program the safe HR zone based upon information available through internally measured data. For example, if the device detects TWA at a HR at which previously no significant TWA was measurable, it automatically adjusts the safe HR zone. The adjusted safe HR zone excludes heart rates at which the device measured significant levels of TWA. As noted above, the changes in IMD measured TWA or ischemia (through T wave and ST segment analysis) are merely surrogate markers for the fact that the patient's condition has changed such that the safe HR zone may be different and may need adjustment. Definitive diagnosis of the HR threshold for TWA or ischemia still requires external testing using external ECG electrodes—"gold standard" TWA or stress testing. One aspect of the device is that it does not require the IMD to be as sensitive or accurate for detection of TWA or ischemia as gold standard techniques, since it is only being used as a surrogate marker for a change in clinical baseline, and not for definitive diagnosis of TWA or ischemia. More detailed description of the operation of the IMD is provided below.

As an example, a patient undergoes external TWA testing and is found to have a significant TWA at heart rate of 110 beats per minute (bpm). The upper HR threshold of the safe HR zone is programmed to be equal or approximately about 110 bpm. In some embodiments, IMD measured TWA is different from externally measured TWA. For the purposes of illustration, assume that in this case the significant TWA is detected by the IMD at HR greater than 140 bpm. Even though the IMD measured TWA is at 140 bpm, the IMD maintains the safe HR zone at the HR threshold determined by the gold standard external testing (110 bpm). However, upon further patient follow up, if the IMD measures TWA occurring at HR above 120 bpm (a change from previously measured HR of 140 bpm), the IMD determines that the patient's condition has changed and alerts a clinician for repeat testing with external ECG electrode techniques. In this aspect, the IMD measured TWA functions as an indicator to confirm whether there has been a change in clinical baseline. Therefore, clinicians do not reset the upper boundary of the safe HR zone to 120 bpm (the HR at which we detect TWA through the IMD) simply based on the new IMD measured HR at which TWA occurs. In some embodiments, the clinicians retest the patient using external ECG electrodes. Based on the results obtained from the external testing, if the clinician determines that the safe HR has indeed drifted and needs readjustment, the processor 12 may be programmed by the physician or technician via the transceiver 16. In certain embodiments the device upon detecting a shift in the safe HR zone may automatically adjust the safe HR zone as described above.

A safe HR zone may be determined in a number of different ways and the determination methods may depend on the disease process one is attempting to minimize risk from. For example, in the case of cardiac arrest and ventricular arrhythmias, a safe HR zone may be determined through TWA testing. The presence and the amount of TWA, which may increase the risk of cardiac arrest, are also known to increase with rising heart rate. Therefore, the heart rate above which the risk for cardiac arrest increases may be determined by obtaining the heart rate at which a patient begins to develop pathological TWA. By providing a system for monitoring and maintaining a patient's HR below this critical level, the patient's risk for cardiac arrest may be minimized. By consistently maintaining the heart rate below a critical level at which physiological changes (TWA) occur that facilitate ventricular arrhythmia and cardiac arrest, the IMD provides an effective preventive care.

In certain embodiments, the safe HR zone is defined by setting the HR at which a significant amount of alternans appears (onset heart rate) as the upper limit for the safe HR zone. If the patient's HR exceeds the onset heart rate, the IMD 10 responds by taking one of several actions depending on the IMD set-up, including: a) recording HR data as outside the safe HR zone, and/or b) emitting an audible alert for the patient to seek medical attention, and/or c) automatically transmitting data to the clinician.

In one implementation, the IMD may reduce the risk of cardiac arrest in patients without significant TWA. More specifically, the maximum HR that the patient achieves during the stress testing without the presence of TWA is called the maximum negative HR. In other words, there exist no significant TWA below the maximum negative HR but the presence of TWA above the maximum negative HR is unknown. In such cases, the maximum negative HR sets the upper limit of the safe HR zone. The difference between the patient's maximum daily heart rate and the maximum negative heart rate can be tracked to monitor the likelihood of adverse clinical outcome; the greater the difference between the maximum negative heart rate and the patient's maximum daily heart rate, the less likely for the patient to develop cardiac arrest.

The IMD may also be used for patients with exercise-induced ischemia. In one implementation, a safe HR zone is determined by subjecting a patient to a cardiac stress test and observing the heart rate at which ischemia develops. ST segment abnormalities, ischemic symptoms, or ischemic wall motion abnormalities may indicate the development of ischemia. The heart rate at which ischemia develops defines the upper limit of the safe zone within certain tolerance levels. Maintaining the patient's HR below this threshold level with medication may prevent complications from ischemia, including angina, arrhythmias, heart failure and infarction.

The system described herein relates to identifying a safe HR zone and maintaining the HR within the safe HR zone. However, the system may be applied to any condition in which the risk of disease complication occurs at higher heart rates. The system may provide clinically useful information in guiding the patient therapy if the threshold HR at which the risk manifests itself can be determined.

It has been observed that ischemia can induce measurable TWA. In certain embodiments, TWA measurement is used to facilitate the diagnosis of ischemia. Changes in ischemic burden may cause changes in TWA, which in some cases may be more sensitive than conventional ST segment monitoring, especially when measured through an IMD. Generally, the amplitude of TWA increases with increasing HR of any individual. Therefore, comparing the TWA amplitude at various times to determine increased risk of ischemia is of limited value. Therefore, HR needs to be adjusted before determining whether there has been a change in the ischemic threshold. In other words, HR adjusted TWA compares the amount of TWA at a given HR as opposed to across heart rates. Specifically, increased HR adjusted TWA may indicate progressive coronary ischemia.

It is also known that TWA at a cellular level is related to calcium overload and mirrors many aspects of the cellular physiology of heart failure. In some embodiments, the HR adjusted TWA level may be used as an indicator of the severity or progression of heart failure. For example, if the HR adjusted TWA is increasing, this may indicate progression of heart failure or volume overload. In some embodiments, the TWA level in a patient with known heart failure is tracked to monitor heart failure status and potentially detect heart failure exacerbations earlier so that appropriate medication (e.g., diuretics) is administered, resulting in a preventive drug therapy for more effective management of adverse cardiac conditions.

Figure 2:
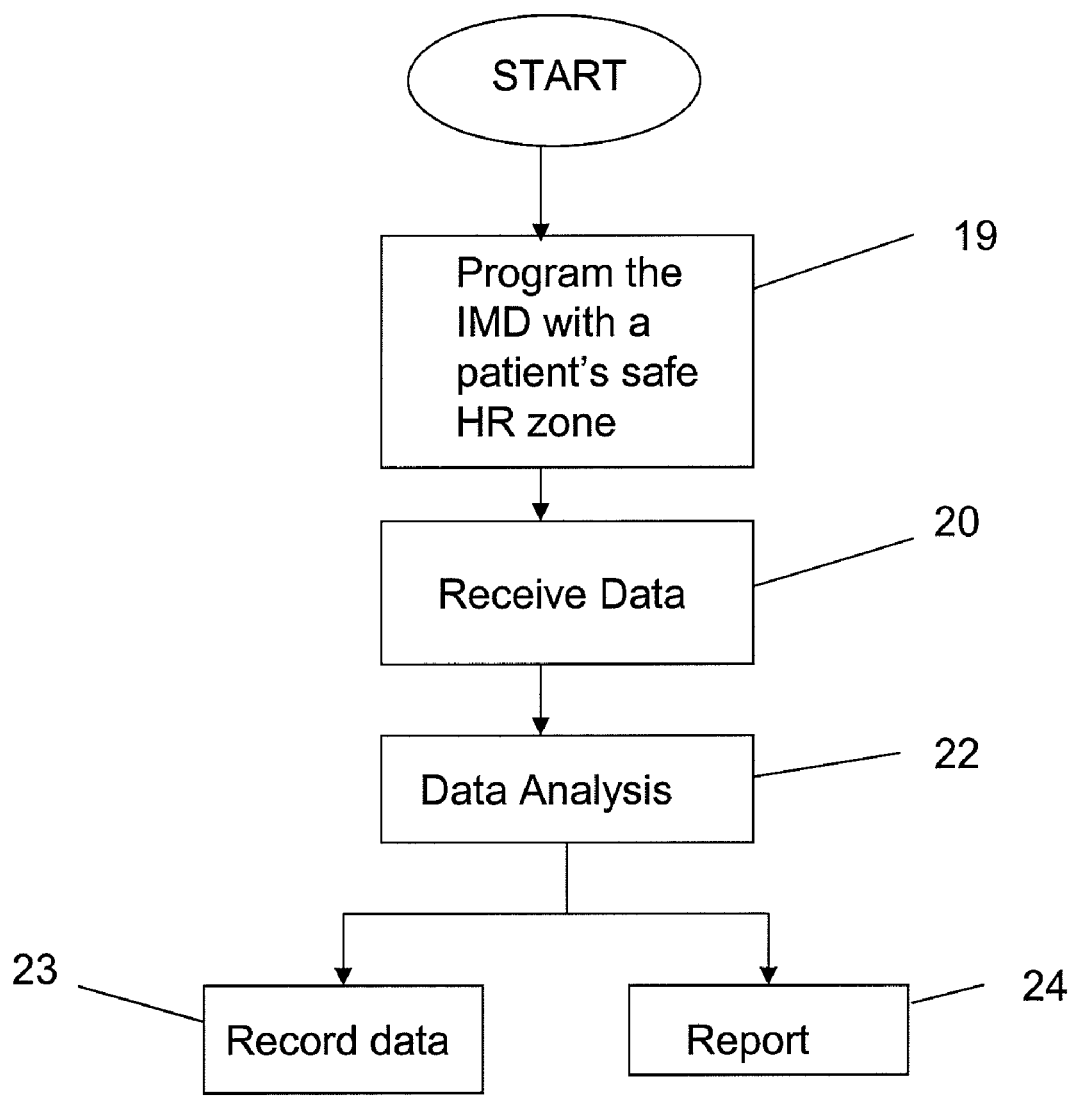
FIG. 2 is a flow chart describing an overview of the operation of an embodiment of the present invention.

Turning to the operation of the IMD 10, FIG. 2 is a flow chart illustrating an exemplary operation the IMD 10. The IMD 10 runs continuously to monitor the patient's HR. Prior to operating the IMD, at step 19, the processor 12 in the IMD 10 is programmed with the patient's safe HR zone. As the IMD 10 continuously receives the heart rate of a patient (step 20), the processor 12 compares the received heart rate to the safe HR zone defined. If the patient's HR has exceeded the safe HR zone (step 22), the processor sends a signal to the transceiver 16 to send an alert to a patient or a clinician (at step 24). In some embodiments, using the transceiver 16, the clinician may reprogram a new HR zone by reprogramming the processor 12. In certain embodiments, the processor 12 may send the result of the comparison between the patient's daily heart rate and the safe HR zone to the memory 14 of the IMD to be stored (step 23).

The process depicted in FIG. 2 may also be used to determine if the safe HR zone has drifted. In such case, rather than simply comparing the patient's HR to the safe HR zone, the IMD 10 may receive and evaluate a surrogate marker of a certain cardiac condition. In the case of arrhythmias, the surrogate marker may be the presence or the amount of TWA. As the TWA data is received continuously in the sensor 11, the processor 12 of the IMD 10 determines if there has been a change in the TWA level. The transceiver 16 in communication with the processor 12 may alert a patient or a clinician for potential repeat testing of the safe HR zone. In the case of ischemia, ST segment deviation may be the surrogate marker and the same process may be applied to determine if the safe HR zone has drifted in the patient. In some embodiments, these surrogate markers are used to indicate whether there has been a change in the patient's safe HR zone and not necessarily as definitive diagnosis for TWA or ischemia.

Some of the advantageous aspects of the described method over the existing methods for managing heart rate dependent medical conditions include the following without limitation: 1) identification of patient specific safe HR zones and ensuring that a patient lives within the identified safe HR zone reduces risk for adverse clinical events; 2) information provided by the IMD allows clinicians to titrate medical therapy with greater accuracy, specifically with respect to maintaining HR below the predefined upper limits that may overlap with normal heart rates that would otherwise not trigger device alerts, 3) improvements on accuracy of risk assessment for ventricular arrhythmias through determination of the proportion of time a patient's heart rate exceeds the safe HR zone; in the case of an ICD treated patient, such information could guide medical therapy to reduce the likelihood of ICD shocks, 4) capability of the IMD to detect drifts in the safe HR zone allows for early detection of changing clinical substrate and need for clinical reevaluation and/or diagnostic testing.

Figure 3:
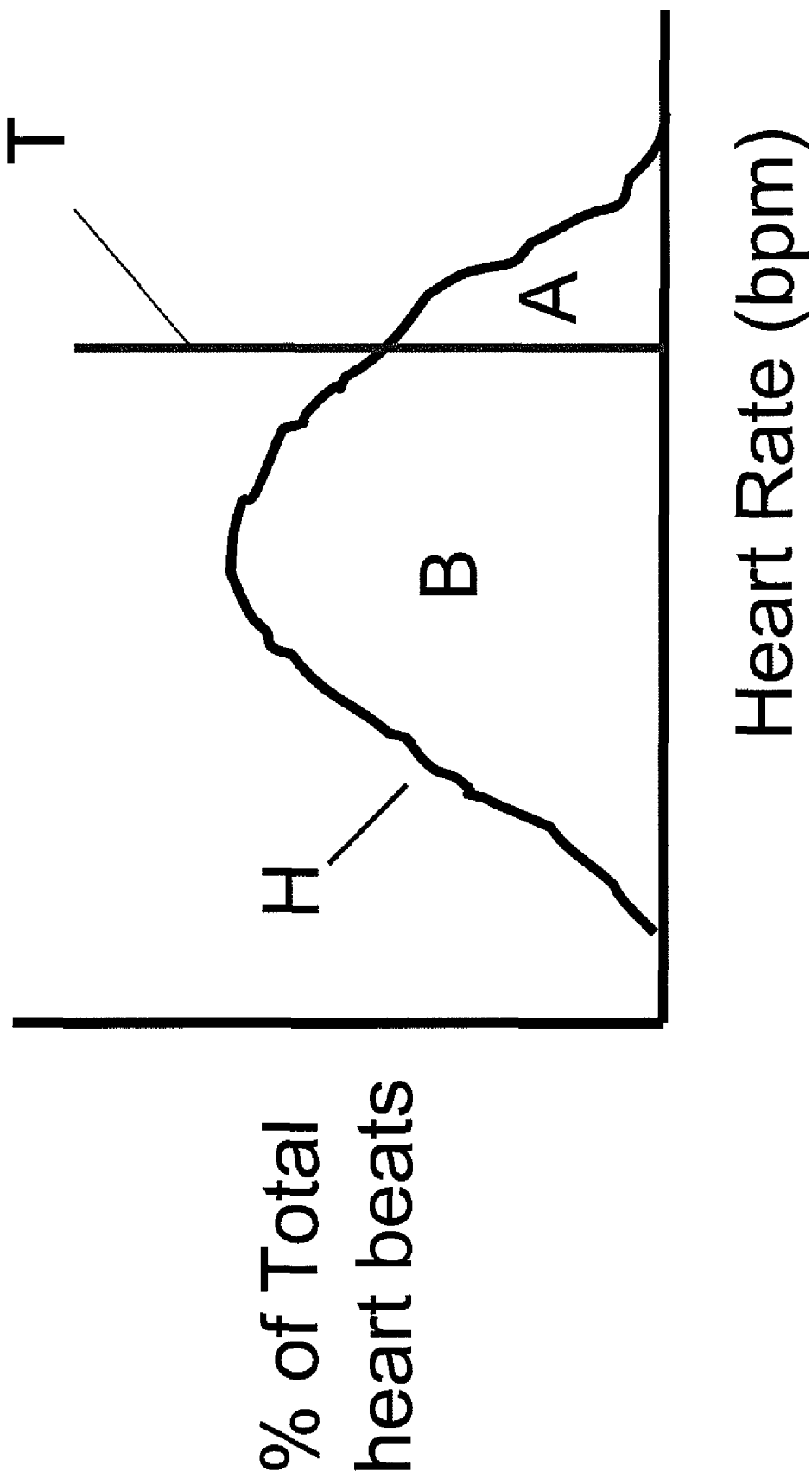
FIG. 3 is a graphical depiction of a patient's heart rate having a heart rate threshold for T-wave alternans.

FIG. 3 is a graph illustrating a patient's heart rate plot with a safe heart rate zone defined by the heart rate at which TWA occurs, also referred to as a TWA threshold (labeled T in FIG. 3). FIG. 3 shows the relationship between the percentage of total heart beats with respect to heart rate. Risk for adverse cardiac condition is quantified by the area under the curve H (FIG. 3) to the right of the TWA threshold (defined by area A). In some embodiments, area A may indicate the amount of time that the patient is under the risk of adverse cardiac condition. Area B shows the safe HR zone for this particular patient. In some embodiments, a value of risk burden, defined by the amount or proportion of time the patient's HR is above the prescribed safe HR zone, is calculated by comparing the area A with respect to the total area under the curve H. More specifically, the risk burden is equal to Area A/(Area A+Area B)×100%. In some embodiments, the processor 12 analyzes the patient's heart rate data to compute the amount of time the patient heart rate spends outside the safe HR zone and sends the data to a clinician via transceiver 16.

Figure 4:
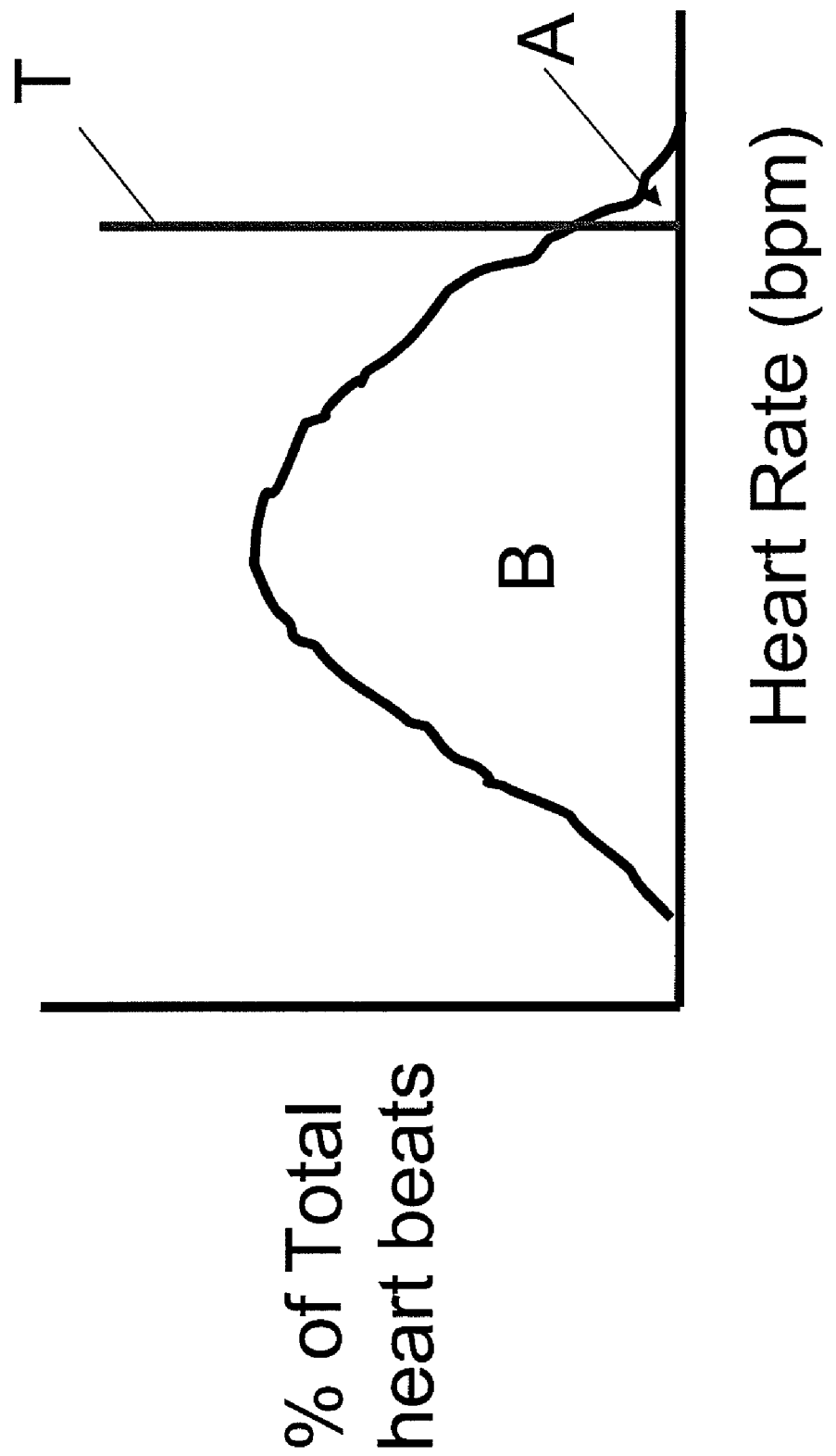
FIG. 4 is a graphical depiction of a patient's heart rate after modifying the drug therapy to lower the patient's heart rate.

Based on the risk quantified by the IMD, a clinician administers appropriate medication to lower the HR so that the patient's HR remains within the safety HR zone. In some embodiments, the IMD and the methods described herein may also provide a tool for assessing the effectiveness of drug therapy. FIG. 4 shows a plot of the heart rate of the hypothetical patient depicted in FIG. 3 following administration of HR slowing medication. As shown, the proportion of the time that the patient's HR exceeds the safe zone is greatly reduced. In this respect, the IMD uses TWA threshold and medical therapy to monitor and prevent adverse cardiac condition as opposed to simply indicating whether the risk for adverse cardiac condition exists or not. In some embodiments, the processor 12 of the IMD 10 outputs the patient's cardiac condition graphically (e.g., plots shown in FIGS. 3 and 4).

Figure 5:
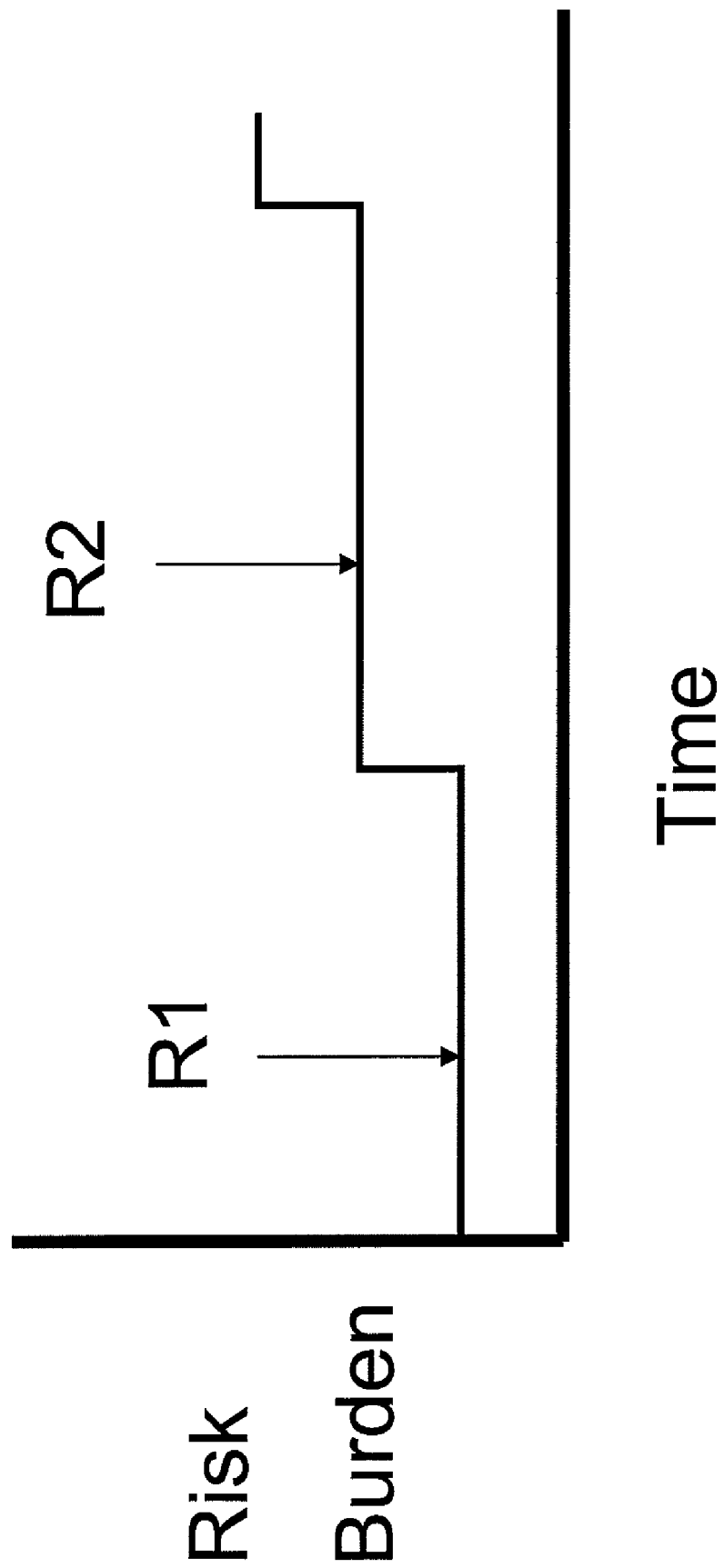
FIG. 5 shows one embodiment of a graphical output based on operation of the implantable medical device.

FIG. 5 shows one embodiment of a graphical output based on operation of the IMD. More specifically, FIG. 5 shows the relationship between the risk burden with respect to time. As noted above, the IMD 10 transmits the patient's heart rate information and the heart rate threshold via transceiver 16 (FIG. 1) to a remote terminal (not shown). A clinician utilizes such data to assess the patient's current cardiac condition. The clinician may include the patient's plot in the patient's overall medical record. Following a subsequent visit to the clinician or a drug therapy, the clinician requests to download the heart rate related information from the IMD and compares it against previously recorded HR data including the HR data before the drug therapy. As an example, FIG. 5 shows point R1 representing a risk burden value (e.g., 10) at the initial clinical visit and point R2 representing a risk burden value (e.g., 25) at a subsequent clinical visit. As shown, the data uploaded from the IMD and the processing of such data to compute and plot the risk burden values over time allows a clinician to see the patient's cardiac condition in snapshot-like manner. In some embodiments, a chart as shown in FIG. 5 may be used to facilitate medical treatment to minimize heart rates outside the safe zone.

The IMD and methods described herein provide a prevention device against sudden death and heart attack by monitoring and maintaining the patient's heart rate within the safe HR zone. By preventing the heart rate from rising to the range where adverse clinical outcome is likely to occur, a clinician reduces the chance of sudden death or heart attack more efficiently.

It is to be understood that while the systems and methods have been described in conjunction with the various illustrative embodiments, the forgoing description is intended to illustrate and not limit the scope of the invention. Other aspects, advantages, and modifications are within the scope of the following claims. All references cited herein are incorporated by reference in their entirety and made part of this application.

What is claimed is:

1. An implantable system for monitoring a cardiac condition of a patient, comprising:
   a sensor for receiving a patient's heart rate and for monitoring at least one of T wave alternans and ST segment deviation; and
   a processor coupled to the sensor, the processor being programmable to set a patient's safe heart rate zone, and the processor configured to:
      identify a change in at least one of the monitored T wave alternans and the monitored ST segment deviation, and
      in response to the identified change, reprogram the safe heart rate zone.

2. The system of claim 1, wherein the system further comprises a transceiver, coupled to the processor, for sending an alert in response to the identified change, and for receiving information from a clinician.

3. The system of claim 2, wherein the received information from the clinician includes information for readjusting the patient's safe heart rate zone, and wherein the processor is configured to adjust the safe heart rate zone based on the received information.

4. The system of claim 3, further comprising surface electrocardiogram (ECG) electrodes for retesting a patient in response to the alert, the retesting comprising evaluating the overall cardiac condition of the patient.

5. The system of claim 4, wherein the safe heart zone is reprogrammed if the retesting using the surface ECG electrodes confirms the occurrence of T wave alternans within the current safe heart rate zone.

6. The system of claim 4, wherein the safe heart rate zone is reprogrammed if the retesting using the surface ECG electrodes confirms that the patient has ischemia.

7. The system of claim 1, wherein the safe heart rate zone is defined by a patient's heart rate at above which the risk of adverse cardiac condition clinically increases.

8. The system of claim 1, wherein the safe heart rate zone is defined by a patient's heart rate at above which abnormal changes to an electrocardiogram (ECG) occur.

9. The system of claim 8, wherein the abnormal changes to the ECG include at least one of T wave alternans and ST segment depression.

10. The system of claim 1, wherein the processor wirelessly transmits to a clinician the patient's heart rate when the heart rate exceeds the safe heart rate zone.

11. The system of claim 1, wherein the processor alerts a clinician or patient when drift occurs in the safe heart rate zone.

12. The system of claim 1, wherein the processor is configured to determine whether the patient's heart rate has exceeded the safe heart rate zone.

13. The system of claim 12, wherein the system further comprises a memory for storing the duration of time that the patient's heart rate has exceeded the safe heart rate zone.

14. The system of claim 1, wherein the processor automatically reprograms the safe heart rate zone if a T wave alternans is detected at a heart rate within the safe heart rate zone.

15. A method of managing a heart rate dependent medical condition comprising:
   programming a processor of an implantable medical device with a patient's safe heart rate zone;
   sensing a patient's heart rate with the implantable medical device;
   monitoring, with the implantable medical device, at least one of T wave alternans and ST segment deviation;
   identifying a change in at least one of the monitored T wave alternans and the monitored ST segment deviation; and
   reprogramming the implantable medical device with a new safe heart rate zone in response to identifying the change.

16. The method of claim 15, comprising comparing the patient's heart rate to the safe heart rate zone and transmitting to a remote terminal the result of the comparison between the patient's heart rate and the safe heart rate zone.

17. The method of claim 15, comprising alerting a clinician when the patient's heart rate falls outside of the safe heart rate zone.

18. The method of claim 17, comprising, in response to the alert, retesting the patient using a standard technique for evaluating the overall cardiac condition of the patient.

19. The method of claim 18, wherein the standard technique is a test using surface ECG electrodes.

20. The method of claim 19, comprising reprogramming the safe heart rate zone only when the surface ECG electrode test confirms that the patient has significant T wave alternans within the current safe heart rate zone.

21. The method of claim 17, comprising modifying a medical therapy to maintain the patient's heart rate within the safe heart rate zone.

22. The method of claim 15, wherein the heart rate dependent condition is risk of cardiac arrest.

23. The method of claim 22, further comprising determining the increased risk of cardiac arrest by observing daily heart rate in excess of the onset heart rate for significant T wave alternans.

24. The method of claim 22, wherein the risk of cardiac arrest is indicated by a decrease in the difference between the patient's daily heart rate and a maximum negative heart rate.

25. The method of claim 22, wherein the risk of cardiac arrest is indicated by an overlap between daily heart rate and a maximum negative heart rate.

26. The method of claim 15, wherein the heart rate dependent medical condition is cardiac ischemia.

27. The method of claim 26, wherein an upper heart rate that defines the safe heart rate zone is determined by observing the heart rate at which clinical ischemia develops during stress testing.

28. The method of claim 26, comprising modifying a medical therapy based on data received from the implantable medical device to maintain the patient's heart rate within the safe heart rate zone.

29. The method of claim 26, further comprising determining increased amount of cardiac ischemia by observing increased heart rate adjusted T wave alternans.

30. The method of claim 26, further comprising determining increased risk of cardiac ischemia by observing increased heart rate adjusted T wave alternans.

31. The method of claim 15, wherein the heart rate dependent medical condition is heart failure.

32. The method of claim 31, comprising determining potential progression of heart failure by observing increased heart rate adjusted T wave alternans.

33. The method of claim 32, comprising alerting a clinician when the patient's heart rate falls outside the safe heart rate zone.

34. The method of claim 15, further comprising determining a drift in the safe heart rate zone by observing changes in a surrogate marker measured by the implantable medical device.

35. The method of claim 34, wherein the heart rate dependent condition is arrhythmias and the surrogate marker is implantable medical device measured T wave alternans.

36. The method of claim 34, wherein the heart rate dependent condition is ischemia and the surrogate marker is implantable medical device measured ST segment deviation.

37. The method of claim 15, comprising calculating a risk burden value of a patient by determining the proportion of time that the patient's heart rate is outside the safe heart rate zone and plotting the risk burden value against time.

38. The method of claim 15, further comprising determining whether the patient's heart rate has exceeded the safe heart rate zone.

39. The method of claim 38, further comprising storing, in a memory of the implantable medical device, the duration of time that the patient's heart rate has exceeded the safe heart rate zone.

40. The method of claim 15, further comprising sending an alert in response to identifying the change.

41. The method of claim 15, further comprising:
receiving, at the implantable medical device, information from a clinician that includes information for readjusting the safe heart rate zone; and
adjusting the safe heart rate zone based on the received information.

42. A computer-readable storage medium comprising instructions that cause a processor of an implantable medical device to:
store a patient's safe heart rate zone;
sense a patient's heart rate;
monitor at least one of T wave alternans and ST segment deviation;
identify a change in at least one of the monitored T wave alternans and the monitored ST segment deviation; and
reprogram a new safe heart rate zone in response to identifying the change.

43. The computer-readable storage medium of claim 42, comprising instructions for alerting a clinician when the patient's heart rate falls outside of the safe heart rate zone.

44. The computer-readable storage medium of claim 42, comprising instructions for reprogramming the safe heart rate zone only when a treadmill test confirms that the patient has significant T wave alternans within the current safe heart rate zone.

45. The computer-readable storage medium of claim 42, comprising modifying a medical therapy to maintain the patient's heart rate within the safe heart rate zone.

* * * * *